United States Patent [19]

Taylor et al.

[11] Patent Number: 4,695,658

[45] Date of Patent: Sep. 22, 1987

[54] ARYL CARBOXYLATE PROCESS

[75] Inventors: Edward C. Taylor, Princeton; Alan H. Katz, Cranbury; Randy A. Bull, Hopewell; Lance R. Byers, Hightstown; Richard A. Brown, Trenton, all of N.J.

[73] Assignee: FMC Corporation, Philadelphia, Pa.

[21] Appl. No.: 589,257

[22] Filed: Mar. 12, 1984

[51] Int. Cl.$^4$ .................. C07C 39/10; C07C 69/76
[52] U.S. Cl. ............................. 568/763; 560/108; 560/109; 560/130; 560/138; 568/768; 568/781
[58] Field of Search ............ 560/108, 109, 130, 131, 560/109; 560/130; 560/130; 568/768; 568/781

[56] References Cited

U.S. PATENT DOCUMENTS

| | | | |
|---|---|---|---|
| 2,799,695 | 7/1957 | Taves | 560/55 |
| 3,028,410 | 4/1962 | Zimmer | 568/768 |
| 4,112,243 | 9/1978 | Nowak et al. | 568/768 |
| 4,164,510 | 8/1979 | Dai | 560/55 |
| 4,182,915 | 1/1980 | Harvey | 568/716 |
| 4,207,265 | 6/1980 | Carleton | 568/385 |
| 4,332,963 | 6/1982 | Lyons et al. | 560/131 |
| 4,346,249 | 8/1982 | Krabbenhoft | 568/782 |

FOREIGN PATENT DOCUMENTS 2918592 11/1980 Fed. Rep. of Germany ...... 560/130
7807749 1/1979 Netherlands ........................ 560/109

OTHER PUBLICATIONS

McKellop, A., and Taylor, E. C., *Chemistry in Britain*, "Thallium in Organic Synthesis", vol. 9, No. 4 (1973) pp. 4 to 11.

Taylor, E. C. et al., "Thallium in Organic Synthesis XV, Synthesis of Phenols and Aromatic Nitriles," *J.A.C.S.*, 92, pp. 3520–3522 (1970).

Taylor, E. C. et al., "Thallium in Organic Synthesis XXIII, Elec. Aromatic Thallation", *J.A.C.S.*, 93:19 (Sep. 22, 1971) pp. 4845–4850.

*Primary Examiner*—Werren B. Lone
*Attorney, Agent, or Firm*—Richard E. Elden; Eugene G. Horsky; Eugene G. Seems

[57] ABSTRACT

A process for replacing an aromatic carbon-thallium bond with a carbon-oxygen bond. The process is particularly suitable for producing specific aromatic isomers by thallating an aromatic compound and replacing the thallium with a carboxylate group which can be further hydrolyzed if desired to form an aromatic hydroxyl compound.

15 Claims, No Drawings

ARYL CARBOXYLATE PROCESS

This invention is a process which replaces a carbon-thallium bond of an aromatic compound with a carbon-oxygen bond.

The use of thallium(III) as an oxidizing agent in aromatic oxidations has been well documented by A. McKillop and E. C. Taylor, *Chemistry in Britain*, Volume 9, No. 4 (1973) pages 4 to 11. Replacement of the thallium of a carbon-thallium bond with oxygen would provide a new and useful route to the preparation of aryl esters, and on hydrolysis, phenols. However, a barrier to development of such a process is the difficulty in cleaving the carbon-thallium bond of an arylthallium compound to result in the formation of a carbon-oxygen bond. One process has been published which uses thallium salts to yield a hydroxylated aromatic. The reaction of arylthallium compounds with $Pb(OCOCF_3)_4$ to ultimately yield phenols is described in E. C. Taylor, et al, "Thallium in Organic Syntheses. XV. Synthesis of Phenols and Aromatic Nitriles", *Journal of American Chemical Society*, Volume 92 (1970) page 3520. The arylthallium compound is transmetallated with Pb(IV) and the hydroxylation process is actually a reaction of the aryllead compound.

Another process to cleave a carbon-thallium bond is found in U.S. Pat. No. 4,182,915 to Harvey which discloses contacting an arylthallium with a nucleophilic substituent in a alkaline or neutral solvent. The solvent may be the nucleophile itself, or one which does not react adversely with the system; the type or amount of solvent used is not critical. Harvey also teaches the use of a promoter containing either a combined iodine atom or containing copper in either the zero valence state or in any higher valence state. Even at the preferred high temperatures and high pressures, the reaction rates of the Harvey process are so slow that extended reaction times are required, even at elevated temperatures and pressures. The process of Harvey also has the disadvantage of producing a mixture of products including aniline, phenol, and phenyl iodide.

According to the present invention, an improved process is provided to replace a carbon-thallium bond of an arylthallium compound with a carbon-oxygen bond. The process comprises the steps of forming a nonaqueous solution containing the arylthallium compound, a nitrile, a carboxylic acid or salt, and sufficient acid to maintain an excess of free acid in the solution during the reaction, dissolving a cuprous compound in the solution, and reacting the solution thereby replacing thallium moiety with the carboxylate moiety to form substantially only an aryl carboxylate ester of the corresponding arylthallium compound.

It is within the general scope of this invention that the aryl carboxylate ester so formed can be hydrolyzed thereby forming the corresponding aromatic hydroxy compound. The hydrolysis may be accomplished by any convenient means, such as acid hydrolysis, basic hydrolysis, or hydrolysis with water at an elevated temperature and pressure.

Although any arylthallium compound can be used in the present process, it will be evident to one skilled in the art that the invention represents a convenient method of producing desired isomers relatively free of undesired by-products. For example, toluene can readily be thallated to form primarily p-tolyl-thallium as an intermediate. The latter can be converted by the present process to form substantially only a p-tolyl carboxylate which can optionally be hydrolyzed to form p-cresol. Similarly, cumene can be converted to hydroquinone substantially free of the ortho- or meta- isomers by forming the intermediate compound, p-isopropylphenylthallium bistrifluoroacetate and reacting it to form a p-hydroperoxyisopropylphenyl carboxylate which is cleaved by the well-known autoxidation process to form acetone and p-hydroxyphenyl carboxylate. The latter can be hydrolyzed to form hydroquinone substantially free from undesired by-products.

In the more generalized statement of this method to form hydroquinone, the arylthallium compound is a p-alkylphenylthallium compound and the alkyl moiety is capable of being oxidized to form a hydroperoxyalkyl moiety with the added steps of autoxidizing the p-alkylphenyl carboxylate ester formed thereby forming a p-hydroperoxyalkylphenyl carboxylate and cleaving the hydroperoxyalkyl moiety to form a p-hydroxyphenyl carboxylate which may be hydrolyzed to form hydroquinone. Alternatively, according to U.S. Pat. No. 4,207,265, p-cumyl carboxylate can be first hydrolyzed to p-isopropylphenol which can be dehydrogenated to p-isopropenylphenol. The latter is known to form p-hydroperoxyisopropylphenol which is known to be cleaved by known methods to form acetone and hydroquinone.

In a more generalized form of the above alternative embodiment of the process to form hydroquinone, the arylthallium compound is a p-alkylphenylthallium compound and the alkyl moiety is capable of being dehydrogenated to form an α-βalkenyl moiety with the added steps of hydrolyzing the p-alkylphenyl carboxylate thereby forming a p-alkylphenol, dehydrogenating the p-alkylphenol to a p-alkenylphenol, reacting the p-alkenylphenol with at least an equimolar amount of hydrogen peroxide in the presence of glacial acetic acid and a catalytic amount of a strong acid whereby there is obtained hydroquinone and acetone.

Taylor et al, in "Thallium in Organic Synthesis. XXIII. Electrophilic Aromatic Thallation. Kinetics and Applications to Orientation Control in the Synthesis of Aromatic Iodides," *Journal of American Chemical Society*, Volume 93 (1971) pages 4845–4850, disclose that the thallation of aromatic compounds can be highly sterically specific. For example, the thallium addition to cumene is 94% para. However, at elevated temperatures, such as by refluxing at 73° C. in trifluoroacetic acid, the meta isomer will predominate. On the other hand, thallation of methylbenzoate yields 95% of the ortho isomer. Therefore, by selecting conditions, the preferred steric isomer distribution can be controlled. For example, by refluxing p-cumylthallium compound, the predominate isomer will be m-cumylthallium compound which can be used to produce resorcinol or any suitable intermediate compound without undesired by-product formation.

In the more generalized statement of this process to form resorcinol, the arylthallium compound is a m-alkylphenylthallium compound wherein the alkyl moiety is capable of either being autoxidized to form the m-alkylphenyl carboxylate ester which is cleaved to form a m-hydroxyphenyl carboxylate or alternatively the alkyl moiety is capable of being dehydrogenated to form an α-βalkene with the added steps of hydrolyzing the m-alkylphenyl carboxylate thereby forming a m-alkylphenol, dehydrogenating the m-alkylphenol to a m-alkenylphenol, reacting the m-alkenylphenol with at least an equimolar amount of hydrogen peroxide in the presence of glacial acetic acid and a catalytic amount of a strong acid whereby there is obtained resorcinol and acetone.

Any convenient nonaqueous solvent for the reaction may be used which will not react adversely with any of the reactants or depress the yields of the reactions. The solvent may be one of the reactants, such as the carboxylic acid. On the other hand, it may be convenient to carry out the present reaction in the same solvent in which the arylthallium compound is formed. It is not necessary for the solution to be anhydrous.

Thallation of monoalkylbenzenes takes place under common thallation conditions. These conditions include the reaction of thallium(III) trifluoroacetate with an aromatic compound in trifluoroacetic acid at room temperature. Other thallic salts of strong organic acids can be used, such as the acetates, methanesulfonates, trifluoromethanesulfonates, and naphthalenesulfonates. Other solvents suitable for thallation reactions may also be used, such as $CCl_4$ or nitrile solvents, including acetonitrile or benzonitrile. Also suitable are combinations of these solvents with trifluoroacetic acid (TFA) or with one another. Temperatures ranging from room temperature to the refluxing temperature of the solvent are suitable. Other thallation conditions have been described in the literature, any one of which is suitable for preparing thallated monoalkylbenzenes.

It is essential that the solvent system for the cleavage reaction contains a nitrile for reasons which will be explained later. The nitrile is desirably present in the solvent in quantities sufficient to complex the copper(I) present in the reaction mixture; preferably, at least a four-fold excess of the nitrile should be present.

The presence of carboxylate salt or carboxylic acid is essential in the solvent system for reasons which will become clear subsequently. The amount of carboxylic acid required is generally at least the molar equivalent of the thallium compound. Larger amounts are suitable. The acid can be any carboxylic acid, including acetic, benzoic, propionic, and trifluoroacetic acid. The added carboxylate salts can be such that they are soluble in the reaction mixture, including alkali metal carboxylates. It is often convenient to use a carboxylic acid as at least part of the solvent.

Sufficient acid must be present in the solution to ensure that an excess of acid is present throughout the reaction.

A copper(I) compound is essential in the solution. The reaction mechanism has not been established for certain. However, for the purpose of this application it is convenient to assume that the copper(I) reduces the arylthallium compound forming a thallium(I) compound and an aryl radical. The resulting copper(II) can then oxidize the aryl radical to the aryl cation which then reacts with the carboxylate anion. Therefore, the copper(I) need not be required in a stoichiometric relationship in the reaction mixture. The copper(I) compound may be any copper(I) compound that is capable of forming a carboxylate salt under the reaction conditions. If a copper(I) carboxylate, such as acetate or benzoate or any other carboxylate is used, it is not necessary to have additional carboxylate ions present. The copper(I) compounds must be soluble in a nitrile solvent that contains a carboxylic acid or carboxylate salt, including cuprous chloride, cuprous bromide, and cuprous nitrate. Cuprous oxide may be used if sufficient acid is available. The amount of the copper(I) compound used can vary from a large excess to a catalytic amount with respect to the arylthallium compound. Reaction rates are favorable with approximately stoichiometric quantities of copper(I).

It is essential that the solvent system contains a nitrile because coordinated nitrile ligands stabilize copper(I) against oxidation to copper(II).

The temperature of the reaction can vary from room temperature to 100° C. (or the reflux temperature of the solvent). Higher temperatures are preferred since temperatures near room temperature result in very slow reaction rates. It is usually not necessary to pressurize the reactants but if a temperature higher than the boiling point of the reaction mixture is desired the system may be pressurized.

The aryl carboxylate formed in the cleavage reaction can be isolated by distillation. It can also be recovered by washing the reaction mixture with water to remove copper and thallium salts and any other water soluble components, such as carboxylic acids and carboxylate salts, and subsequently the product which remains can be purified by distillation.

It was unexpectedly found that by providing a carboxylic acid in a nonaqueous acid solution containing dissolved copper(I) that the prior art problems for breaking a carbon-thallium bond were alleviated. Prior art methods using a halide form an aryl halide product and an insoluble thallium(I) halide, the process of Harvey, using neutral or alkaline solutions in the presence of copper or iodide promoters, invariably yields a mixture of two or more products. As illustrated previously, the present process is suitable to replace a carbon-thallium bond with a carbon-oxygen bond. The ester moiety which replaces the thallium can be conveniently converted to many other useful functional groups to form useful products, such as phenols and hydroquinone, without the formation of undesirable by-products.

Another advantage of the present process is the ability to recycle the thallium and copper. The metal salts from the arylthallium cleavage reaction are dissolved in water. Any copper(I) will oxidize to copper(II) in air. The addition of HCl results in the precipitation of highly insoluble thallous chloride and the formation of water soluble cupric chloride. The thallous chloride may be reoxidized to the desired thallic salt.

The copper(II) can be recovered by precipitation as the sulfide followed by conversion to $Cu_2O$ or other copper salts using common chemical, electrochemical, or metallurgical techniques.

The following examples are presented to enable one skilled in the art to practice the invention and are not intended to limit the invention.

EXAMPLE 1

PREPARATION OF p-ISOPROPYLPHENYLTHALLIUM BISTRIFLUOROACETATE

A flask was charged with 5 ml trifluoroacetic acid (TFA) and 1.5 ml (10.8 mmol) cumene. A solution of 5.5 g (10.1 mmol) thallium(III) tristrifluoroacetate in 15 ml TFA was slowly added. The mixture was stirred for 18 hours at room temperature. The solvent was evaporated from the reaction mixture leaving a dark-green tar. After four addition and evaporation cycles, using 30 ml dichloroethane to remove residual TFA, a green solid was obtained. This was washed with $CH_2Cl_2$ and an off-white solid collected by filtration. After drying in air, 3.5 g (6.4 mmol) p-isopropylphenylthallium bistrifluoroacetate resulted for a 63.4% yield.

EXAMPLE 2

CLEAVAGE OF CARBON-THALLIUM BOND WITH CUPROUS TRIFLUOROACETATE

The product from Example 1 (0.97 g, 1.8 mmol) was dissolved in 15 ml CH$_3$CN and deoxygenated with a nitrogen purge. The acidity was reduced to pH 4 according to commercial pH test paper. Cuprous oxide (0.15 g, 2.1 mmol) was dissolved, also under nitrogen, in 5 ml CH$_3$CN by adding 0.5 ml TFA. This was added to the p-isopropylphenylthallium bistrifluoroacetate solution. The mixture was adjusted to pH 4–5 and was heated at reflux for eight hours. A 14% yield of 4-isopropylphenol product was obtained after hydrolysis of the trifluoroacetate ester.

EXAMPLE 3

CLEAVAGE OF CARBON-THALLIUM BOND WITH CUPROUS ACETATE

The product from Example 1 (1.37 g, 2.49 mmol) was dissolved in 20 ml CH$_3$CN and deoxygenated with a nitrogen purge. Cuprous acetate (0.31 g, 2.49 mmol) was added. The mixture was adjusted to pH 4–5 and heated at reflux under nitrogen for six hours. Analysis of the reaction mixture by GC showed a 78% yield of 4-isopropylphenol, formed from the hydrolysis of the acetate ester.

Pursuant to the requirements of the patent statutes, the principle of this invention has been explained and exemplified in a manner so that it can be readily practiced by those skilled in the art, such exemplification, includes what is considered to represent the best embodiment of the invention. However, it should be clearly understood that, within the scope of the appended claims, the invention may be practiced by those skilled in the art, and having the benefit of this disclosure, otherwise than as specifically described and exemplified herein.

What is claimed is:

1. The process of replacing a carbon-thallium bond of an arylthallium compound with a carbon-oxygen bond comprising:
    a. forming a nonaqueous solution containing the arylthallium compound, a nitrile, a carboxylic acid or salt thereof, and an acid in an amount sufficient to maintain an excess of free acid in the solution, and
    b. adding to the nonaqueous solution a cuprous copper compound which is capable of forming a soluble carboxylate salt therein, and which serves to promote the replacement of the thallium moiety with the carboxylate moiety to form substantially only an arylcarboxylate ester of the corresponding arylthallium compound.

2. The process of claim 1 with the added step of hydrolyzing the aryl carboxylate ester to form an arylhydroxy compound.

3. The process of claim 1 wherein the arylthallium compound is a p-alkylphenylthallium compound whereby a p-alkylphenyl carboxylate is formed.

4. The process of claim 2 wherein the arylthallium compound is a p-alkylphenylthallium compound whereby a p-alkylphenol is formed.

5. The process of claim 1 wherein the arylthallium compound is a p-alkylphenylthallium compound and the alkyl moiety is capable of being oxidized to form a hydroperoxyalkyl moiety with the added steps of autoxidizing the p-alkylphenyl carboxylate ester formed thereby forming a p-hydroperoxyalkylphenylalkyl carboxylate and cleaving the hydroperoxyalkyl moiety to form a p-hydroxyphenyl carboxylate.

6. The process of claim 5 with the added step of hydrolyzing the p-hydroxyphenyl carboxylate thereby forming hydroquinone.

7. The process of claim 1 wherein the arylthallium compound is a p-alkylphenylthallium compound and the alkyl moiety is capable of being dehydrogenated to form an α-β alkenyl moiety with the added steps of hydrolyzing the p-alkylphenyl carboxylate thereby forming a p-alkylphenol, dehydrogenating the p-alkylphenol to a p-alkenylphenol, reacting the p-alkenylphenol with at least an equimolar amount of hydrogen peroxide in the presence of glacial acetic acid and a catalytic amount of a strong acid whereby there is obtained hydroquinone and acetone.

8. The process of claim 1 wherein the arylthallium compound is a m-alkylphenyl thallium compound whereby a m-alkylphenyl carboxylate is formed.

9. The process of claim 2 wherein the arylthallium compound is a m-alkylphenylthallium compound whereby a m-alkylphenol is formed.

10. The process of claim 1 wherein the arylthallium compound is a m-alkylphenylthallium compound wherein the alkyl moiety is capable of being oxidized to form a hydroperoxyalkyl moiety with the added steps of autoxidizing the m-alkylphenyl carboxylate ester formed thereby forming a m-hydroperoxyalkylphenyl carboxylate and cleaving the hydroperoxyalkyl moiety to form a m-hydroxyphenyl carboxylate.

11. The process of claim 10 with the added step of hydrolyzing the m-hydroxyphenyl carboxylate thereby forming resorcinol.

12. The process of claim 1 wherein the arylthallium compound is a m-alkylphenylthallium compound wherein the alkyl moiety is capable of being dehydrogenated to form an α-β alkene with the added steps of hydrolyzing the m-alkylphenyl caboxylate thereby forming a m-alkylphenol, dehydrogenating the m-alkylphenol to a m-alkenylphenol, reacting the m-alkyenylphenol with at least an equimolar amount of hydrogen peroxide in the presence of glacial acetic acid and a catalytic amount of a strong acid whereby there is obtained resorcinol and acetone.

13. The process of manufacturing hydroquinone comprising:
    a. reacting a thallium compound with a monoalkylbenzene having the alkyl moiety capable of being dehydrogenated to form an α-β alkene, thereby forming a p-alkylphenylthallium compound,
    b. forming a nonaqueous solution containing said p-alkylphenylthallium compound, a carboxylic acid or salt thereof, a nitrile, an acid in an amount sufficient to maintain an excess of acid in the reaction solution and a copper (I) compound, which is capable of forming a soluble carboxylate salt therein and which serves to promote the replacement of the thallium moiety with a carboxylate moiety thereby forming a p-alkylphenyl carboxylate,
    c. oxidizing the p-alkyl moiety and cleaving same thereby replacing same with a first hydroxyl moiety, and
    d. hydrolyzing the carboxylate moiety thereby replacing same with a second hydroxyl moiety.

14. The process of manufacturing resorcinol comprising:
   a. reacting a thallium compound with a monoalkylbenzene having the alkyl moiety capable of being dehydrogenated to form an α-β alkene, thereby forming a p-alkylphenylthallium compound,
   b. heating the p-alkylphenylthallium compound thereby forming a m-alkylthallium compound,
   c. forming a nonaqueous solution containing said m-alkylphenylthallium compound, a carboxylic acid or salt thereof, a nitrile, an acid in an amount sufficient to maintain an excess of acid in the reaction solution and a copper (I) compound which is capable of forming a soluble carboxylate salt therein, and which serves to promote the replacement of the thallium moiety with a carboxylate moiety thereby forming a m-alkylphenyl carboxylate,
   d. oxidizing the m-alkyl moiety and cleaving same thereby replacing same with a first hydroxyl moiety, and
   e. hydrolyzing the carboxylate moiety thereby replacing same with a second hydroxyl moiety.

15. The process of replacing a carbon-thallium bond of an isopropylphenylthallium compound with a carbon-oxygen bond comprising:
   a. forming a nonaqueous solution containing the isopropylphenylthallium compound, acetonitrile, acetic acid or salt thereof, and an acid in an amount sufficient to maintain an excess of free acid in the solution,
   b. adding to the nonaqueous solution a cuprous copper compound which is soluble therein and which serves to promote the replacement of the thallium moiety with the acetate moiety to form substantially only isopropylphenyl acetate.

* * * * *